(12) United States Patent
Hieronymi et al.

(10) Patent No.: US 8,258,314 B2
(45) Date of Patent: Sep. 4, 2012

(54) PROCESS FOR THE PREPARATION OF SUBSTITUTED HETEROAROMATICS

(75) Inventors: Antje Hieronymi, Köln (DE); Lars Rodefeld, Leverkusen (DE)

(73) Assignee: SALTIGO GmbH, Langenfeld, DE (US)

( * ) Notice: Subject to any disclaimer, the term of this patent is extended or adjusted under 35 U.S.C. 154(b) by 266 days.

(21) Appl. No.: 12/663,536

(22) PCT Filed: May 27, 2008

(86) PCT No.: PCT/EP2008/056442
§ 371 (c)(1),
(2), (4) Date: May 4, 2010

(87) PCT Pub. No.: WO2008/151920
PCT Pub. Date: Dec. 18, 2008

(65) Prior Publication Data
US 2010/0217015 A1    Aug. 26, 2010

(30) Foreign Application Priority Data
Jun. 9, 2007 (DE) .......................... 10 2007 026 763

(51) Int. Cl.
*C07D 405/00* (2006.01)
(52) U.S. Cl. ..................................... 548/517
(58) Field of Classification Search .............. 548/517
See application file for complete search history.

(56) References Cited

U.S. PATENT DOCUMENTS
2006/0155134 A1    7/2006 Werner et al.

OTHER PUBLICATIONS
Kumada, et al.; Tetrahedron 1982, 38, 3347-3354.
Zimmer, et al.; Synth. Commun. 1986, 16, 689-696.

*Primary Examiner* — Taofiq A Solola
(74) *Attorney, Agent, or Firm* — Michael A. Miller

(57) ABSTRACT

A process is described for the preparation of substituted heteroaromatics of the general formula (I)

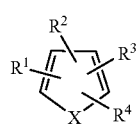

(I)

where
X is oxygen, sulphur or $NR^5$ where $R^5$ is hydrogen, $C_1$-$C_{20}$-alkyl or $C_5$-$C_6$-aryl and
$R^4$ is $C_1$-$C_{20}$-alkyl, $C_5$-$C_6$-aryl or heteroaryl,
$R^1$, $R^2$, $R^3$ is hydrogen, halogen, $C_1$-$C_{20}$-alkyl, $C_5$-$C_6$-aryl or heteroaryl, by reaction
A) of a halogenated heteroaromatic of the general formula (II)

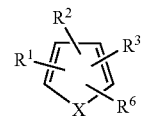

(II)

where
X has the meaning given for formula (I) and
$R^6$ is bromine, iodine or chlorine and
$R^1$, $R^2$ and $R^3$ have the meaning given for formula (I), with a Grignard reagent of the general formula (III)

$$R^4MgHal \qquad (III)$$

where
$R^4$ has the meaning given for formula (I) and
Hal is bromine, iodine or chlorine or
B) reaction of the halogenated heteroaromatics of the formula (II) with magnesium firstly to give a Grignard compound of the general formula (IIIa)

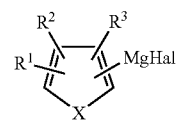

(IIIa)

where
Hal is bromine, iodine or chlorine and
X and $R^1$, $R^2$ and $R^3$ have the meaning given for formula (I),
and further reaction with a halogenated compound of the general formula (IV)

$$R^4Hal \qquad (IV)$$

where
$R^4$ has the meaning given for formula (I) and
Hal is bromine, iodine or chlorine,
where the reactions A) or B) are in each case carried out in the presence of an Ni or Pd catalyst, characterized in that the process is carried out in the presence of cycloalkyl alkyl ether as solvent and optionally a further solvent.
Likewise described is the use of cycloalkyl alkyl ethers, in particular cyclopentyl methyl ether, in the Kumada reaction for the preparation of substituted heteroaromatics, in particular substituted thiophenes.

6 Claims, No Drawings

PROCESS FOR THE PREPARATION OF SUBSTITUTED HETEROAROMATICS

The present invention relates to a process for the preparation of substituted heteroaromatics. The improvement over the processes known hitherto consists in the improvement in the selectivity.

Substituted heteroaromatics are valuable intermediates in the electronic industry. They are used, for example, in the application areas of illumination, solar cells and displays and create new possibilities as regards design, processing and energy efficiency. Compared to established products, they moreover offer economic incentives since their preparation is significantly less complex. In particular, on account of their property of building up conjugated double bonds after polymerization, thiophenes can be used in various structural elements of the specified applications.

The first process for the preparation of substituted heteroaromatics starting from halogenated aromatics and Grignard reagents was developed by Kumada et al. (*Tetrahedron* 1982, 38, 3347-3354). Here, a wide variety of alkyl and aryl radicals were introduced into various positions of thiophenes, pyridines and quinolines. Polyalkylations were also carried out by reacting polyhalogenated heteroaromatics with Grignard compounds with nickel catalysis. Diethyl ether was used as solvent for these reactions. Disadvantages are not only the use of the low-boiling diethyl ether which has a strong tendency to form peroxide, but also that in this process significant amounts of the homocoupling products (e.g. dithiophene in the case of the reaction of 3-bromothiophene with n-hexylmagnesium bromide) are formed, which make further purification difficult.

Furthermore, *Synth. Commun.* 1986, 16, 689-696 by Zimmer et al. describes the Kumada coupling of bromothiophene with alkylmagnesium halides. Here, inter alia, the coupling of 3-bromothiophene with n-hexylmagnesium bromide is carried out in diethyl ether; the authors obtained an isolated yield of 71%.

US 2006/0155134 discloses that Kumada couplings of 3-halothiophenes with alkyl- and arylmagnesium halides can be carried out in methyltetrahydrofurans. The procedure in this solvent reduces the by-product spectrum compared with the processes which use e.g. diethyl ether or tetrahydrofuran. A disadvantage of this process is that isomeric, branched secondary components are produced in the order of magnitude around 0.5%.

US 2006/0155134 describes that the use of tert-butyl methyl ether during the described Kumada coupling of an alkyl radical onto 3-halothiophenes produces a poor result with regard to the secondary component spectrum, in particular in the formation of dithiophenes.

It was an object to develop an improved process for the preparation of substituted heteroaromatics which leads to fewer secondary components.

The invention therefore provides a process for the preparation of substituted heteroaromatics of the general formula (I)

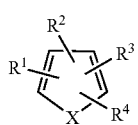

(I)

where
X is oxygen, sulphur or $NR^5$ where $R^5$ is hydrogen, $C_1$-$C_{20}$-alkyl or $C_5$-$C_6$-aryl and
$R^4$ is $C_1$-$C_{20}$-alkyl, $C_5$-$C_6$-aryl or heteroaryl,
$R^1$, $R^2$, $R^3$ is hydrogen, halogen, $C_1$-$C_{20}$-alkyl, $C_5$-$C_6$-aryl or heteroaryl, by reaction
A) of a halogenated heteroaromatic of the general formula (II)

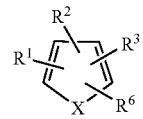

(II)

where
X has the meaning given for formula (I) and
$R^6$ is bromine, iodine or chlorine and
$R^1$, $R^2$ and $R^3$ have the meaning given for formula (I),
with a Grignard reagent of the general formula (III)

$R^4MgHal$ (III)

where
$R^4$ has the meaning given for formula (I) and
Hal is bromine, iodine or chlorine or
B) reaction of the halogenated heteroaromatics of the formula (II) with magnesium firstly to give a Grignard compound of the general formula (IIIa)

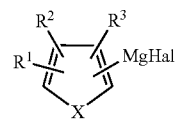

(IIIa)

where
Hal is bromine, iodine or chlorine and
X and $R^1$, $R^2$ and $R^3$ have the meaning given for formula (I), and further reaction with a halogenated compound of the general formula (IV)

$R^4Hal$ (IV)

where
$R^4$ has the meaning given for formula (I) and
Hal is bromine, iodine or chlorine,
where the reactions A) or B) are in each case carried out in the presence of an Ni or Pd catalyst, characterized in that the process is carried out in the presence of cycloalkyl alkyl ether as solvent and optionally one or more further solvents.

The cycloalkyl alkyl ether is preferably cyclopentyl methyl ether.

The catalyst used is a nickel or palladium compound, preferably a nickel(II) chloride, particularly preferably [1,3-bis(diphenylphosphino)propane]nickel(II) chloride, in a stoichiometry of 0.001-20 mol %, preferably 0.05-1.5 mol %, particularly preferably 0.1-0.5 mol %.

Magnesium is used in a stoichiometry of 80-150 mol %, preferably 100-140 mol %, particularly preferably 105-130 mol %.

The alkyl halide or aryl halide of the general formula (IV) forming the Grignard reagent has a stoichiometry of 80-150 mol %, preferably 100-140 mol %, particularly preferably 105-130 mol %.

The solution of the Grignard reagent of the general formula (III) should have a concentration of 0.1-4 mol/l, preferably 0.5-4 mol/l, particularly preferably 1.5-3.5 mol/l.

The process according to the invention is, as is customary in the case of Grignard reactions, carried out under inert conditions. For example, the apparatus used for the reaction is heated if required and filled with nitrogen or argon. The inert atmosphere is maintained also during the addition of raw materials and the removal of samples, where in particular freedom from water is to be respected.

In the present process, magnesium is preferably initially introduced into cyclopentyl methyl ether in a synthesis apparatus. Here, the magnesium can be used, for example, in the form of pieces, filings, granules or powder or mixtures of these use forms. The concentration of magnesium in cyclopentyl methyl ether according to the invention is 0.1-4 mol/l, preferably 0.5-4 mol/l, particularly preferably 1.5-3.5 mol/l. It is also possible to initially introduce magnesium into a mixture of cyclopentyl methyl ether with another solvent, for example, but not limited to: toluene, but also ethers such as tetrahydrofuran, methyltetrahydrofuran, tert-butyl methyl ether or diethyl ether or mixtures of the aforementioned solvents.

An alkyl halide or aryl halide of the general formula (IV) or (II) as described above is then reacted with the magnesium to give a Grignard reagent of the formula (III) or (IIIa). Here, alkyl is an alkyl group having $C_1$-$C_{20}$, preferably $C_4$-$C_{20}$, particularly preferably $C_4$-$C_{10}$ and aryl is preferably of the formula (II), particular preference being given to using monohalogenated, alkylated thiophenes or dihalogenated dithiophenes. In both cases, the halogens are preferably chlorine, bromine or iodine, particularly preferably bromine.

The alkyl halide or aryl halide can be added pure or diluted in a solvent. Solvents are, for example, cyclopentyl methyl ether, tetrahydrofuran, methyltetrahydrofuran, tert-butyl methyl ether, diethyl ether, toluene or mixtures of the aforementioned solvents. The molarity of the Grignard reagent is preferably 0.5-4 mol/l, particularly preferably 1.5-3.5 mol/l.

The general properties of Grignard reagents apply for Grignard reagents used in the process according to the invention. They are sensitive to air and water and should thus be handled and stored under a nitrogen atmosphere or noble gas atmosphere. Storage should generally be kept as short as possible, i.e. the Grignard reagents should if possible be freshly prepared. Furthermore, the reaction of Grignard reagents with water is highly exothermic and hydrogen is released. For this reason, containers of Grignard reagents should be protected against the entry of water.

The Grignard reagents of the formula (III) or (IIIa) used in the process according to the invention enter in the course of the reaction into a transition-metal-catalysed reaction with a halide of the general formula (IV) or a halogenated heteroaromatic of the general formula (II) having the radicals as described above. Here, the halogen of the halide is replaced by the corresponding group of the Grignard reagent. Preference is given here to reaction A) in which $R^6$ is exchanged for $R^4$ from the Grignard reagent.

The catalyst for the process described in this invention can be nickel or palladium in oxidation state 0 or II, i.e. Ni(II), Ni(0), Pd(II) or Pd(0). For this process, preference is given to [1,3-bis(diphenylphosphino)propane]nickel(II) chloride and nickel dichloride and mixtures thereof or suspensions of one of the catalysts or suspensions of mixtures of these catalysts. It is also possible to use further preferred nickel catalysts from the group consisting of: nickel(II) acetate, [1,2-bis(diphenylphosphino)ethane]nickel(II) chloride, hexaamminenickel (II) chloride, nickel(II) acetylacetonate, or complexes of nickel(II) acetylacetonate with tri-tert-butylphosphine, 1,3-bis(2,4,6-trimethylphenyl)imidazolidinium chloride, 1,3-bis(2,6-diisopropylphenyl)imidazolidinium chloride, 1,3-diadamantylimidazolium chloride, triadamantylphosphine, 1,3,4-triphenyl-4,5-dihydro-1H-1,2,4-triazol-5-ylidene, 1,1'-bis(diphenylphosphino)ferrocene, 2-(dicyclohexylphosphino)biphenyl, and also combinations of all of the aforementioned catalysts and their suspensions. In the process of the present invention, particular preference is given to the use of [1,3-bis(diphenylphosphino)propane]nickel(II) chloride in the form of a suspension or as pure feed material.

In the present invention, e.g. [1,3-bis(diphenylphosphino)propane]nickel(II) chloride is added as solid or suspension to the Grignard solution prepared as described above. It is also possible to add the Grignard solution to a suspension of the catalyst in cyclopentyl methyl ether or another suitable solvent such as tetrahydrofuran, methyltetrahydrofuran, tert-butyl methyl ether, dioxane, toluene or diethyl ether or mixtures of all of the aforementioned solvents. Also, the halogenated heteroaromatic may already be dissolved in this suspension. In the particularly preferred procedure, however, [1,3-bis(diphenylphosphino)propane]nickel(II) chloride without further solvent is metered into the Grignard reagent. The amount of catalyst required is between 0.001-20 mol %, preferably 0.05-1.5 mol %, particularly preferably 0.1-0.5 mol %. The concentration of the possible catalyst suspension is between 20 and 80% by weight in the suitable solvent.

The reaction of the Grignard reagent with the halide $R^4$Hal of the above-described general formula (IV) is initiated by adding the halide to the mixture, prepared as described above, of Grignard reagent with catalyst. It can likewise be brought about by adding the Grignard reagent to a mixture of the halide and catalyst in cyclopentyl methyl ether or a mixture of cyclopentyl methyl ether and a further solvent. In the present procedure, preference is given to the dropwise addition of a halogenated heteroaromatic to a mixture of the corresponding Grignard reagent and [1,3-bis(diphenylphosphino)propane] nickel(II) chloride in cyclopentyl methyl ether.

Preferably, X in formula (I), (II) and (IIIa) is sulphur, i.e. the halide of the formula (II) used is preferably a substituted or unsubstituted halothiophene, preferably a chlorothiophene, bromothiophene or iodothiophene, particularly preferably bromothiophene, very particularly preferably 3-bromothiophene. It can be used pure or in solvents, for example toluene, cyclopentyl methyl ether, tert-butyl methyl ether, diethyl ether, tetrahydrofuran or methyltetrahydrofuran.

The ratio of Grignard reagent to halogenated heteroaromatic can be 80-150 mol %, preference being given to using 100-140 mol %, particularly preferably 105-130 mol %.

$R^1$, $R^2$ and $R^3$ are preferably hydrogen and $R^4$ is preferably a $C_1$-$C_{12}$-alkyl group. $R^4$ is particularly preferably a $C_6$-$C_{10}$- or $C_{12}$-alkyl group (hexyl group, decyl group, dodecyl group). Consequently, thiophenes substituted with a hexyl group, decyl group, dodecyl group, in particular thiophenes substituted in the 3 position, are prepared according to the invention. Here, 3-hexylthiophene is very particularly preferred.

Following initiation of the reaction, the reaction temperature is controlled through the rate of the dropwise addition and counter cooling. The reaction temperature should be between −30 and 106° C. (boiling point of cyclopentyl methyl ether), temperatures are preferably between 10 and 90° C., the temperature fluctuations are particularly preferably between 15 and 70° C.

The process offers an option of converting halogenated heteroaromatics into substituted heteroaromatics in a virtually complete conversion without, in so doing, obtaining isomeric secondary components, such as e.g. in the case of the reaction of 3-bromothiophene with hexylmagnesium bromide the isomer 3-(1-methylpentyl)thiophene, in noteworthy amounts. Surprisingly, during this reaction, when using cyclopentyl methyl ether or mixtures of cyclopentyl methyl ether with other solvents, only very small amounts of dithiophenes are formed. Moreover, compared with the use of methyltetrahydrofurans, the use of cyclopentyl methyl ether offers the advantage that a considerably smaller fraction of the undesired secondary component 3-(1-methylpentyl)thiophene is found in the crude mixture.

Thus, starting from the same batch of n-hexyl bromide, the following comparative values have been found:

| Solvent | 3-(1-Methylpentyl)thiophene | 3-Hexylthiophene | Dithiophene |
| --- | --- | --- | --- |
| Cyclopentyl methyl ether | 0.5 | 95 | 0.0 |
| Cyclopentyl methyl ether | 0.5 | 90.2 | 0.2 |
| Cyclopentyl methyl ether | 0.6 | 86.5 | n.d. |
| 2-Methyltetrahydrofuran | 1.1 | 81.7 | 3.1 |
| 2-Methyltetrahydrofuran | 1.1 | 93.9 | n.d. |

The selectivity of the coupling with regard to the formation of the secondary component 3-(1-methylpentyl)thiophene in the case of the process presented here is clearly superior to that already known.

Furthermore, cyclopentyl methyl ether offers a number of further advantages compared with other ethers. Examples to be mentioned here are the higher boiling point and also the mixing behaviour with water, which is of great importance for organometallic reactions:

|  | Cyclopentyl methyl ether | 2-Methyltetra-hydrofuran | Tetrahydro-furan | tert-Butyl methyl ether | Diethyl ether |
| --- | --- | --- | --- | --- | --- |
| Boiling point [° C.] | 106 | 78 | 65 | 55 | 35 |
| Melting point [° C.] | <−140 | −136 | −108.5 | −108.7 | −116.3 |
| Enthalpy of evaporation [kcal/kg] | 69.2 | 89.7 | 98.1 | 81.7 | 86.08 |
| Azeotrope with water, boiling point [° C.] | 83 | 71 | 64 | — | 34 |
| Solubility in water at 23° C. [% by wt.] | 1.1 | 14 (20° C.) | infinite | 4.8 | 6.5 |
| Solubility of water in solvent at 23° C. [% by wt.] | 0.3 | 4.4 (20° C.) | infinite | 1.5 | 1.2 |

The low tendency to form peroxide also characterizes cyclopentyl methyl ether as a safer-to-handle solvent for the preparation of substituted heteroaromatics, in particular substituted thiophenes.

The invention therefore further provides the use of cycloalkyl alkyl ethers, in particular cyclopentyl methyl ether, in the Kumada reaction for the preparation of substituted heteroaromatics, in particular substituted thiophenes.

EXAMPLES

Example 1

Comparative 19.8 g of hexyl bromide were added dropwise at 50° C. to 2.8 g of magnesium filings in 35 ml of tetrahydrofuran such that an exothermy was continually discernible. After refluxing for two hours, 80 mg of [1,3-bis(diphenylphosphino)propane]nickel(II) chloride were added. Then, at 5° C., 16.3 g of 3-bromothiophene are added dropwise. The mixture is stirred at 23° C. for 16 h, then diluted with 60 ml of tetrahydrofuran and poured onto 10% strength (w/w) hydrochloric acid heat-treated to 0° C. The organic phase is separated off and the aqueous phase is extracted three times with 50 ml of tert-butyl methyl ether. The combined organic phases are washed with in each case 50 ml of water and sodium chloride solution (saturated at 23° C.), dried over 2.0 g of magnesium sulphate, filtered and concentrated by evaporation. A solid (dithiophene) precipitates out of the crude solution and is filtered off. 8.1 g of crude product remains, from which further dithiophene precipitates out following prolonged standing. The supernatant solution has a content of 73%. The following were identified as secondary components: 9% dodecane, 4% 3-(1-methylpentyl)thiophene.

Example 2

Comparative 19.8 g of hexyl bromide were added dropwise at 60-70° C. to 2.8 g of magnesium filings in 35 ml of 2-methyltetrahydrofuran such that an exothermy was continually discernible. After stirring for two hours at 80-85° C., 80 mg of [1,3-bis(diphenylphosphino)propane]nickel(II) chloride were added. Then, at 15-20° C., 16.3 g of 3-bromothiophene are added dropwise. The mixture is stirred for 3 h at 23° C., then the mixture is poured onto 10% strength hydrochloric acid (w/w) heat-treated to 0° C. The organic phase is separated off and the aqueous phase is extracted three times with 50 ml of tert-butyl methyl ether. The combined organic phases are washed with in each case 50 ml of water and sodium chloride solution (saturated at 23° C.), dried over 2.0 g of magnesium sulphate, filtered and concentrated by evaporation. The crude product had the following composition: 11% 3-bromothiophene, 2% dodecane, 1.1% 3-(1-methylpentyl)thiophene, 82% 3-hexylthiophene, 3.1% dithiophene.

Example 3

According to the Invention 19.8 g of hexyl bromide were added dropwise at 90° C. to 2.8 g of magnesium filings in 35 ml of cyclopentyl methyl ether such that an exothermy was continually discernible. After refluxing for two hours, 80 mg of [1,3-bis(diphenylphosphino)propane]nickel(II) chloride were added. Then, at 10° C., 16.3 g of 3-bromothiophene are added dropwise. The mixture is stirred for 2 h at 23° C., then heated at 100° C. for 30 minutes and, after cooling, carefully hydrolysed with 10% strength hydrochloric acid (w/w) heat-treated to 0° C. The organic phase is separated off and the aqueous phase is extracted three times with 50 ml of tert-butyl methyl ether. The combined organic phases are washed with in each case 50 ml of water and sodium chloride solution (saturated at 23° C.), dried over 2.0 g of magnesium sulphate, filtered and concentrated by evaporation. The crude product had the following composition: 2.4% 3-bromothiophene, 7.4% dodecane, 0.6% 3-(1-methylpentyl)thiophene, 86.5% 3-hexylthiophene.

Example 4

Comparative 19.8 g of hexyl bromide were added dropwise at 60-70° C. to 2.8 g of magnesium filings in 35 ml of 2-methyltetrahydrofuran such that an exothermy was continually discernible. After refluxing for two hours, 80 mg of [1,3-bis(diphenylphosphino)propane]nickel(II) chloride in 1 ml of 2-methyltetrahydrofuran were added. Then, at 20° C., 16.3 g of 3-bromothiophene are added dropwise. The mixture is stirred for 16 h at 23° C., then carefully hydrolysed with 10% strength hydrochloric acid (w/w) heat-treated to 0° C. The organic phase is separated off and the aqueous phase is extracted three times with 50 ml of tert-butyl methyl ether. The combined organic phases are washed with in each case 50 ml of water and sodium chloride solution (saturated at 23° C.), dried over 2.0 g of magnesium sulphate, filtered and concentrated by evaporation. The crude product had the following composition: 1.4% 3-bromothiophene, 1.7% dodecane, 1.1% 3-(1-methylpentyl)thiophene, 93.9% 3-hexylthiophene.

Example 5

According to the Invention 121.4 g of hexyl bromide were added dropwise at 80-85° C. to 17.5 g of magnesium filings in 215 ml of cyclopentyl methyl ether such that an exothermy was continually discernible. After stirring for two hours at 80-85° C., 0.49 g of [1,3-bis(diphenylphosphino)propane]nickel(II) chloride in 8 ml of cyclopentyl methyl ether were added. Then, at 15° C., 16.3 g of 3-bromothiophene are added dropwise. The mixture is stirred for 16 h at 23° C., then carefully hydrolysed with 10% strength hydrochloric acid (w/w) heat-treated to 0° C. The organic phase is separated off and the aqueous phase is extracted three times with 50 ml of tert-butyl methyl ether. The combined organic phases are washed with in each case 50 ml of water and sodium chloride solution (saturated at 23° C.), dried over 2.0 g of magnesium sulphate, filtered and concentrated by evaporation. The crude product had the following composition: 0% 3-bromothiophene, 6.5% dodecane, 0.5% 3-(1-methylpentyl)thiophene, 88.2% 3-hexylthiophene.

Example 6

Comparative 19.8 g of hexyl bromide were added dropwise at 60-70° C. to 2.8 g of magnesium filings in 35 ml of tert-butyl methyl ether such that an exothermy was continually discernible. After refluxing for two hours, 80 mg of [1,3-bis(diphenylphosphino)propane]nickel(II) chloride were added. Then, at 20° C., 16.3 g of 3-bromothiophene were added dropwise. The mixture is stirred for 16 h at 23° C. and then carefully hydrolysed with 10% strength hydrochloric acid (w/w) heat-treated to 0° C. The organic phase is separated off and the aqueous phase is extracted three times with 50 ml of tert-butyl methyl ether. The combined organic phases are washed with in each case 50 ml of water and sodium chloride solution (saturated at 23° C.), dried over 2.0 g of magnesium sulphate, filtered and concentrated by evaporation. The crude product had the following composition: 10.3% 3-bromothiophene, 4.7% dodecane, 0.1% 3-(1-methylpentyl)thiophene, 77.4% 3-hexylthiophene, 5.2% dithiophene.

Example 7

According to the Invention 364.5 g of hexyl bromide were added dropwise at 72° C. to 52.3 g of magnesium filings in 645 ml of cyclopentyl methyl ether such that an exothermy was continually discernible. After stirring for two hours at 80-85° C., 1.47 g of [1,3-bis(diphenylphosphino)propane]nickel(II) chloride were added. Then, at 20° C., 309.3 g of 3-bromothiophene were added dropwise. The mixture is stirred for 16 h at 23° C., then 260 ml of toluene are added and then carefully hydrolysed with 10% strength hydrochloric acid (w/w) heat-treated to 0° C. The organic phase is separated off and the aqueous phase is extracted three times with 250 ml of toluene. The combined organic phases are washed with in each case 250 ml of water and sodium chloride solution (saturated at 23° C.), dried over 20 g of magnesium sulphate, filtered and concentrated by evaporation. The crude product had the following composition: 2.2% 3-bromothiophene, 4.1% dodecane, 0.5% 3-(1-methylpentyl)thiophene, 90.2% 3-hexylthiophene, 0.2% dithiophene.

Example 8

According to the Invention 364.5 g of hexyl bromide were added dropwise at 72° C. to 52.9 g of magnesium filings in 632 ml of cyclopentyl methyl ether such that an exothermy was continually discernible. After stirring for two hours at 80-85° C., 1.47 g of [1,3-bis(diphenylphosphino)propane]nickel(II) chloride were added. Then, at 20° C., 309.3 g of 3-bromothiophene are added dropwise. 260 ml of toluene are added. The mixture is then stirred for 16 h at 23° C., then carefully hydrolysed with 10% strength hydrochloric acid (w/w) heat-treated to 0° C. The organic phase is separated off, washed with in each case 250 ml of water and sodium hydrogencarbonate solution (saturated at 23° C.) and concentrated by evaporation. The crude product had the following composition: 0.8% 3-bromothiophene, 3.3% dodecane, 0.5% 3-(1-methylpentyl) thiophene, 95.2% 3-hexylthiophene, 0% dithiophene.

Example 9

According to the Invention 19.8 g of hexyl bromide were added dropwise at 70° C. to 2.8 g of magnesium filings in 35 ml of cyclopentyl methyl ether such that an exothermy was continually discernible. After stirring for two hours at 80-85° C., 80 mg of [1,3-bis (diphenylphosphino)propane]nickel(II) chloride were added at 20° C. Then, at 85° C., 16.3 g of 3-bromothiophene are added dropwise. The mixture is heated to reflux for one hour and then stirred for 16 h at 23° C. The mixture is diluted with toluene and added to 10% strength hydrochloric acid (w/w) heat-treated to 0° C. The organic phase is separated off and the aqueous phase is extracted three times with 50 ml of tert-butyl methyl ether. The combined organic phases are washed with in each case 50 ml of water and sodium chloride solution (saturated at 23° C.), dried over 2.0 g of magnesium sulphate, filtered and concentrated by evaporation. The crude product had the following composition: 6.1% 3-bromothiophene, 4.6% dodecane, 0.6% 3-(1-methylpentyl) thiophene, 84.9% 3-hexylthiophene, 2.5% dithiophene.

Example 10

According to the Invention 364.5 g of hexyl bromide were added dropwise at 72° C. to 52.3 g of magnesium filings in 678 ml of cyclopentyl methyl ether such that an exothermy was continually discernible. After stirring for three hours at 80-85° C., 1.47 g of [1,3-bis (diphenylphosphino)propane]nickel(II) chloride were added. Then, at 20° C., 309.3 g of 3-bromothiophene are added dropwise. The mixture is stirred for 16 h at 23° C., then 260 ml of toluene are added and then the mixture is carefully hydrolysed with 10% strength hydrochloric acid (w/w) heat-treated to 0° C. The organic phase is separated off, washed with in each case 250 ml of water and sodium hydrogencarbonate solution (saturated at 23° C.) and concentrated by evaporation. The crude product had the following composition: 0% 3-bromothiophene, 6.1% dodecane, 0.6% 3-(1-methylpentyl)thiophene, 86.4% 3-hexylthiophene.

Example 11

According to the Invention 364.5 g of hexyl bromide were added dropwise at 72° C. to 52.3 g of magnesium filings in 678 ml of cyclopentyl methyl ether such that an exothermy was continually discernible. After stirring for two hours at 80-85° C., 1.47 g of [1,3-bis (diphenylphosphino)propane]nickel(II) chloride were added. Then, at 20° C., 309.3 g of 3-bromothiophene are added dropwise. 260 ml of toluene are added and the mixture is afterstirred for 4 h at 50° C. and for 12 h at 23° C. The mixture is added to 10% strength hydrochloric acid (w/w) heat-treated to 0° C. The organic phase is separated off, washed with in each case 250 ml of water, sodium hydrogencarbonate solution (saturated at 23° C.) and washed again with water and concentrated by evaporation. The crude product had the following composition: 4.6% 3-bromothiophene, 2.5% dodecane, 0.5% 3-(1-methylpentyl)-thiophene, 86.2% 3-hexylthiophene, 0.2% dithiophene.

Example 12

According to the Invention 646.3 g of hexyl bromide were added dropwise at 70° C. to 95.3 g of magnesium filings in 1098 ml of cyclopentyl methyl ether such that an exothermy was continually discernible. After stirring for three hours at 80-85° C., 2.4 g of [1,3-bis (diphenylphosphino)propane]nickel(II) chloride were added. Then, at 20° C., 491.1 g of 3-bromothiophene are added dropwise. 415 ml of toluene are added and the mixture is afterstirred for 4 h at 50° C. and for 12 h at 23° C. The mixture is added to 10% strength hydrochloric acid (w/w) heat-treated to 0° C. The organic phase is separated off, washed with in each case 780 ml of water, sodium hydrogencarbonate solution (saturated at 23° C.) and again with water and concentrated by evaporation. The crude product had the following composition: 1.3% 3-bromothiophene, 2.6% dodecane, 0.5% 3-(1-methylpentyl)thiophene, 90.6% 3-hexylthiophene, 0% dithiophene.

The invention claimed is:

1. Process for the preparation of substituted heteroaromatics of the general formula (I)

(I)

where

X is oxygen, sulphur or $NR^5$ where $R^5$ is hydrogen, $C_1$-$C_{20}$-alkyl or $C_5$-$C_6$-aryl and $R^4$ is $C_1$-$C_{20}$-alkyl, $C_5$-$C_6$-aryl or heteroaryl, $R^1$, $R^2$, $R^3$ is hydrogen, halogen, $C_1$-$C_{20}$-alkyl, $C_5$-$C_6$-aryl or heteroaryl, by reaction A) of a halogenated heteroaromatic of the general formula (II)

(II)

where

X has the meaning given for formula (I) and $R^6$ is bromine, iodine or chlorine and $R^1$, $R^2$ and $R^3$ have the meaning given for formula (I), with a Grignard reagent of the general formula (III)

$R^4MgHal$ (III)

where $R^4$ has the meaning given for formula (I) and

Hal is bromine, iodine or chlorine or

B) reaction of the halogenated heteroaromatics of the formula (II) with magnesium firstly to give a Grignard compound of the general formula (IIIa)

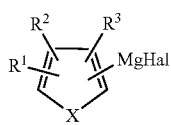 (IIIa)

where
Hal is bromine, iodine or chlorine and
X and $R^1$, $R^2$ and $R^3$ have the meaning given for formula (I),
and further reaction with a halogenated compound of the general formula (IV)

$R^4Hal$ (IV)

where
$R^4$ has the meaning given for formula (I) and
Hal is bromine, iodine or chlorine, where the reactions A) or B) are in each case carried out in the presence of an Ni or Pd catalyst, characterized in that the process is carried out in the presence of cyclopentyl methyl ether as solvent and optionally one or more further solvents.

2. Process according to claim 1 wherein the further solvent is a solvent selected from the group consisting of toluene, tetrahydrofuran, methyltetrahydrofuran, tert-butyl methyl ether, diethyl ether and mixtures thereof.

3. Process according to claim 1, characterized in that it is carried out at a temperature between −30 and 106° C.

4. Process according to claim 1, characterized in that the catalyst is [1,3-bis(diphenylphosphino)propane]nickel(II) chloride.

5. Process according to claim 1, characterized in that X in formula (I), (II) and (IIIa) is sulphur.

6. Process according to claim 1, characterized in that $R^4$ is a $C_6$-$C_{10}$- or $C_{12}$-alkyl radical.

* * * * *